United States Patent [19]

Belkin

[11] Patent Number: 4,680,668
[45] Date of Patent: Jul. 14, 1987

[54] ANTI-STATIC DEVICE

[75] Inventor: Nathan L. Belkin, Clearwater, Fla.

[73] Assignee: Superior Surgical Mfg. Co., Inc., Seminole, Fla.

[21] Appl. No.: 687,381

[22] Filed: Dec. 28, 1984

[51] Int. Cl.⁴ .............................................. A61N 1/14
[52] U.S. Cl. .................................................. 361/220
[58] Field of Search ............... 361/212, 216, 220, 223; 174/5 R, 5 SG, 5 SB

[56] References Cited

U.S. PATENT DOCUMENTS

| | | | |
|---|---|---|---|
| 1,940,491 | 12/1933 | Freitag | 361/223 |
| 3,084,700 | 4/1959 | Fischer et al. | 361/212 |
| 3,211,153 | 10/1965 | Gambetti | 361/232 |
| 3,349,285 | 10/1967 | Belkin | 361/220 |
| 3,596,134 | 10/1968 | Burke | 361/220 |
| 3,857,397 | 12/1974 | Brosseau | 361/220 |
| 4,373,175 | 2/1983 | Mykkanen | 361/220 |
| 4,398,277 | 8/1983 | Christiansen et al. | 361/220 |

*Primary Examiner*—L. T. Hix
*Assistant Examiner*—David M. Gray
*Attorney, Agent, or Firm*—Edward R. Weingram

[57] ABSTRACT

A device for dissipating electrostatic electricity from a person wearing a static protecting garment. The device comprises a means for continuously conducting electricity between the garment and the person; and means for continuously conducting electricity from the garment and person to ground.

The invention is also directed to a method of preventing electrostatic damage to a device which is sensitive to electrostatic potentials, said device being handled by a person wearing a static protective garment. The method comprises simultaneously and continuously grounding the person and the garment.

6 Claims, 4 Drawing Figures 4,680,668

ANTI-STATIC DEVICE

BACKGROUND OF THE INVENTION

1. Field of the Invention

This invention relates generally to electrostatic protective devices, and in general to the protection of electrostatic sensitive equipment from static electricity built-up on clean room and other electrostatic protective garments.

2. Description of the Prior Art

The problem of preventing damage to electronic equipment is a serious one. Electrostatic potentials well below the level of human sensitivity (3.5 KV to 4 KV) can cause failure in bipolar and MOS devices, film resistors, silicon chips and many other electronic components, from early processing through assembly to an electronic system's end of life. These potentials can exist on solids or liquids that are electrically isolated from each other and from ground. The procedures and materials traditionally used for electrostatic devise (ESD) protection are in part designed to ensure that these electrostatic potentials are equalized.

Protective containers such as IC rails, bags, and tote boxes—be they static dissipative ($10^6$–$10^{13}$ ohms /sq) or conductive (less than $10^6$ ohms /sq)-operate by allowing the transfer of static electricity across the material to ground. When transported in an ungrounded condition, however, these containers can still develop static potentials. Therefore, before the contents can be safely handled, either mechanically or by a human operator, the container and handler must be at the same potential. Electrostatic charges can be shared by direct connection or via an intervening material, such as a conductive tabletop. In a typical work station designed for ESD protection, the protective container is placed directly on the grounded work surface, while the operator is usually electrically connected to the work surface and to ground with a conductive wrist strap.

Typically, in such surroundings static protective garments are also worn by the persons handling the electronic devices. These protective garments do not have what may be termed a zero static charge but rather produce or generate a minimum amount of static. The static protective characteristics of the fabric are generally achieved by the introduction of carbon yarn or other conductive yarn into the weave of the basic non-conductive fabric, and/or a topical anti-static finish applied to the garment during routine in-use laundry or dry cleaning processes. The basic non-conductive fabric is typically constructed of continuous filament non-conductive polyester. The routine application of a topical anti-stat, depending on its chemical formulation, can either increase the static dissipative properties of a material or minimize its triboelectric charge generating properties by inhibiting its ability to give up or accept electrons, or both. A preferred static protective fabric is one in which conductive fibers are interwoven into the polyester fibers in a grid design (approx. $\frac{1}{2}$"). One such fabric is sold under the trademark ULTRA-CHIEF 10 by Worklon, a division of Superior Surgical Mfg. Co., Inc.

Many of the static-protective devices known in the art dissipate an electrical charge generated by a person to a ground; see for example the following U.S. patents:

U.S. Pat. No. 4,398,277 to Christiansen et al;
U.S. Pat. No. 4,373,175 to Mykkanen;
U.S. Pat. No. 3,857,397 to Brosseau;
U.S. Pat. No. 3,596,134 to Burke;
U.S. Pat. No. 3,084,700 to Fischer et al; and
U.S. Pat. No. 1,940,491 to Freitag.

Christiansen et al. describes a device which is strapped onto the users wrist to control the electrostatic charge accumulation on the body of a person. Typically, the wrist strap is a conductive polymer for conducting electrostatic charge via the individuals wrist to a ground cord secured to the wrist strap with an electrically conductive snap connection. The wrist strap can be closed by a Velcro, (trademark of Velcro U.S.A., Inc.) fastener to secure the wrist strap to the wrist of the individual wearer. The strap relies on the firm intimate contact of the conductive member to the body or person of the individual.

Mykkanen describes a similar safety apparatus, e.g., wrist strap which is connected between a human and an electrically conductive terminal.

Brosseau also describes an electrically conducive wrist strap worn on the wrist.

Burke describes an apparatus to be worn by persons working in an electrostatic field for eliminating discomfort and ill effects of discharges of electrical energy through the person. The device comprises one or more bands in the form of garter or a belt, each having a flexible conductive element therein which conforms to the body shape and lies close to the skin. The garter belt is connected by leads to a conductor for contacting grounded structures.

Fischer et al. relates to a grounded comb.

Frietag relates to a device for grounding persons working near high-voltage electric power stations to prevent electrocution of or injury to a person.

Thus, it can be seen that all of the aforedescribed devices are directed solely to discharging electrostatic charge from a person.

SUMMARY AND OBJECTS OF THE INVENTION

It is an object of this invention to provide a device which not only discharges static electricity from a person, but discharges static electricity generated by an electrostatic dissipating garment worn by such person.

It is a further object of this invention to provide a device for simultaneously discharging static electricity from a garment worn by a person and from that person, said device being easy to put on and install.

It is still a further object of this invention to provide a device which is simple in construction and inexpensive.

It is an object of this invention to provide a device which prevents the accumulation of static electricity on an electrostatic dissipating garment.

Another object of this invention to provide a device which prevents the accumulation of static electricity on the person or the electrostatic dissipating garment worn by such person without unduly incumbering the person with a multitude of grounding implements.

It is another object of this invention to provide a device which prevents the accumulation of static electricity on the person or the electrostatic dissipating garment in an efficient manner with a minimum of interference to the person, and which includes provisions to minimize harm from accidental contact of the garment with high voltage sources.

Yet another object of this invention to provide a device which contains components which are conductively connected, but which may be replaced if the individual components deteriorate in order to ensure adaquate performance, which is comfortable to wear, and which is durable in operation.

Still another object of this invention to provide a device which provides a means for discharging static electricity generated by the clothing of a person wearing an electrostatic dissipating garment.

A further object of this invention is to provide a device which provides a means to enable people to work in electrostatic free environments without having to remove or alter their clothing to reduce the interaction between themselves and their clothing.

It is another object of this invention to provide a device which provides a means for dissipating electrostatic forces which are developed between a person and his normal clothing or the different layers of the person's normal clothing.

All of the foregoing objects and others are achieved by a device for dissipating electrostatic electricity from a person wearing a static protective garment. The device comprises (a) a means for continuously conducting electricity between the garment and the person; and (b) a means for continuously conducting electricity from the garment or person to a ground.

The invention is also directed to a method of preventing electrostatic damage to a device which is sensitive to electrostatic potentials, said device being handled by a person wearing a static protective garment. The method comprises simultaneously and continuously grounding the person and the garment.

DESCRIPTION OF THE INVENTION

Figure 1:
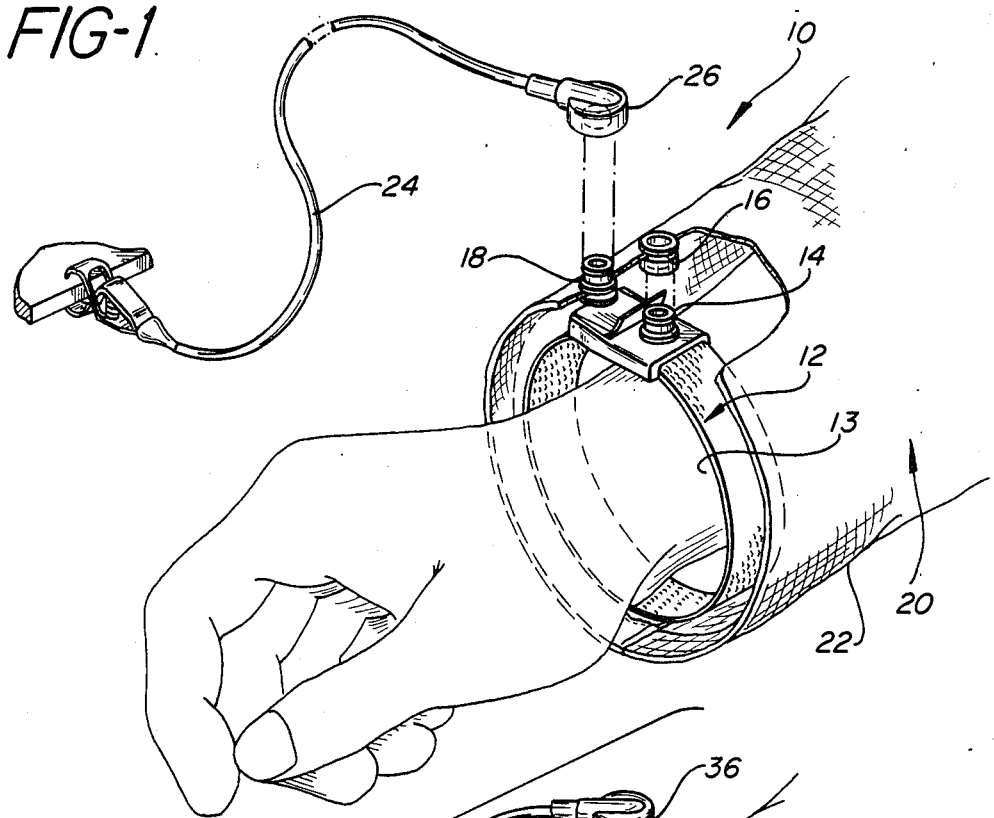
FIG. 1 is one embodiment of the device this invention used for simultaneously dissipating electrostatic electricity from a person and the static protective garment being worn by said person.

None of the known devices in the art relate to both simultaneously grounding a person and grounding the static protective garment worn by that person. In fact, there is no realization in the art that such is required.

It has been found that although the carbon yarns in a static protective fabric are conductive, if the garment is not grounded and since the yarns in the fabric, e.g. polyester, are not conductive, whatever static is generated on these fibers is suspended thereon. Neither the charges on the carbon yarn nor the polyester fiber are dissipated until the person wearing the garment and the garment come in contact with a ground. Thus, while the presence of carbon or any other conductive fiber in the fabric assists in dissiptating the static charge, the polyester therein is not conductive at all and the static charge that is generated on these fibers (which are surrounded by conductive fibers) is suspended in that area. If the fabric has been treated with an anti-static topical finish, for example, during the final rinse cycle of the laundering process and the static is provided with paths to the nearest conductive yarn, i.e. it is dissipated throughout the garment.

Applicant has discovered through tests that a deliberate continuous grounding of both the garment and person is highly desirable and necessary while working with highly sensitive equipment. For example, in one situation an individual donned an anti-static clean room type coverall made of 100% polyester fabric with carbon filament interwoven in a grid design. The fabric, sold in garments under the trademark ULTRA-CHIEF 10, by Worklon, was said to have an anti-static capability (surface resistivity of $1 \times 10^5$ ohms/sq). The person then stepped onto a 1" thick polystyrene insulation material and touched a 5,000 volt DC power supply. The 5/KV E-Field was immediately detected from the outside surface of the suit. When the suit and person were grounded this E-Field instantly disappeared and the individual lost the charge from his person. This test clearly demonstrates the importance of providing a deliberate continuous grounding system for both the garment and the wearer.

The antistatic garment, in theory, acts as a basic Faraday cage. Such a cage effectively shields and protects items from electrical events which occur outside of the cage. To perform this function, it is not necessary that the cage be grounded. It is necessary, however, that all conductive material forming the cage be electrically connected to constitute a single conductor. The resistance of the conductive circuit through the cage must be sufficiently low so that any charge induced at one point on the cage will be conducted to the most distant locations on the cage more rapidly than the charge is induced. This generally accounts for the recommendation that static protective garments have a surface resistivity not exceeding $1 \times 10^5$ ohms/per sq.

However, if a Faraday cage garment is not grounded within itself and contains charged items, the algebraic sum of all the contained charges is inductively coupled to the cage, and a corresponding E-field emanates from the entire outside of its surface. On the other hand, if the cage (garment) is grounded, the entire outer surface has a net charge of zero with respect to the ground and no field emanates from the garment.

Thus, if one of the intended purposes of a clean room static protective garment is to protect external items from any charge existing inside the garment, it follows that the garment itself should be at ground potential. Thus the garment will form a protective Faraday cage which is capable of preventing the garments internal charges from being inductively coupled to items outside the garment.

As previously indicated, it is quite commonplace for persons working on electrostatic sensitive devices to wear grounding straps around their wrists. These "wristlets" are generally made of a material which has a conductive fiber content, i.e. stainless steel or carbon. Typically, a contact is provided on the band to which is affixed a fastener. To this fastener, one end of a grounding cord is secured. A current limiting resistor, e.g. 1 megohm, is normally placed in series with the grounding wire at this point as a safety device to protect the user in the event he inadvertently contacts a fatal power supply voltage. On the other end of the cord is an alligator or bulldog clip which is affixed to a ground at the work station. The static protective garment, to applicant's knowledge, has never been affixed to this mechanism, firstly because there is no manner of accomplishing this and, foremost, there was never a recognition of a need for continuously grounding the garment. Applicant has discovered that there is a need for grounding such anti-static garment and has solved the problem of accomplishing such by grounding both the garment and the person utilizing a means for conducting electricity between the conducting fibers in the garment and the person, in conjunction with a means for transferring the electricity from the conducting fibers in the garment or person to the ground.

Referring to the drawings, FIG. 1 describes one embodiment of the device 10 of this invention. Wristlet 12 is wrapped securely around the wearers wrist 13 and may be similar to any of the aforedescribed wristlets which are well known in the art, except it is modified as described herein. The wristlet 12 has electrically conducting fibers which transfer electricity from the wrist 13 to the wristlet 12. At one end of the wristlet 12 is mounted a male snap connecting means 14. The snap 14 is mounted on the wristlet so as to conduct electricity from the conducting fibers in the wristlet 12 to the snap 14. Attached to the sleeve 22 of antistatic garment 20 is a female snap connecting means 16 which mates with and is electrically connected to snap 14. Snap means 16 is mounted on the sleeve 22 so as to conduct electricity from the conducting fibers in sleeve 22.

An additional male snap connecting means 18 is mounted to the garment sleeve 22 in the same manner as snap 16. A grounding cord 24 is provided with a snap means 26 thereon which mates with snap 18. Thus, the device enables the static electricity from the person and anti-static garment to be continuously at the same potential and grounded.

Figure 2:
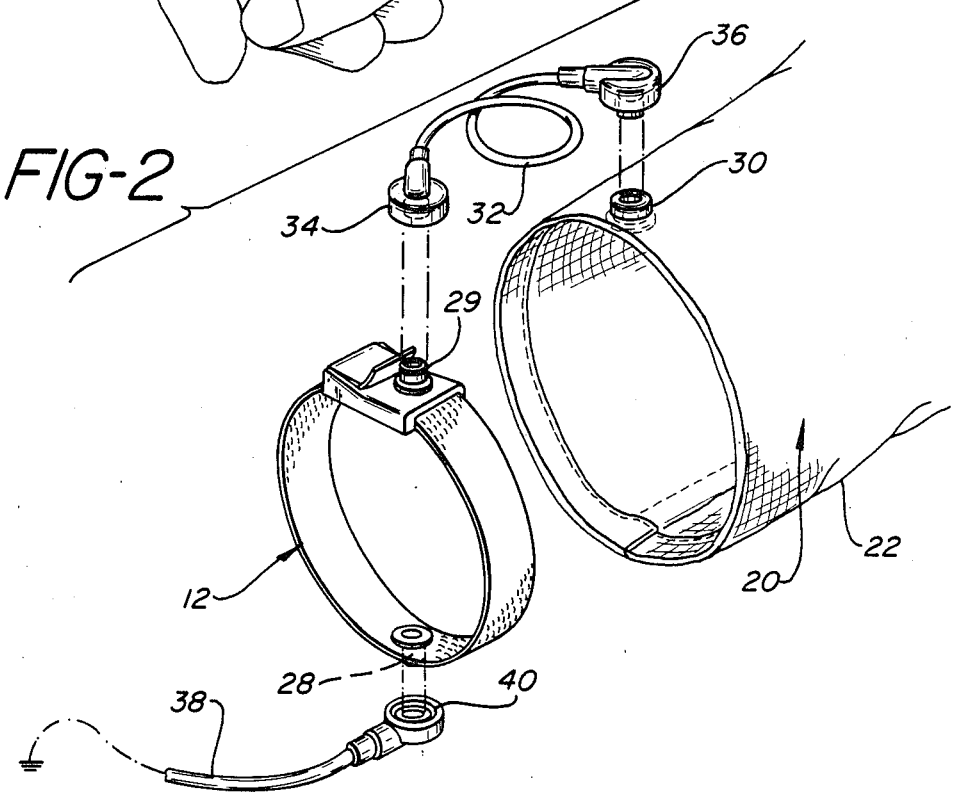
FIG. 2 is another embodiment of such a device.
Figure 3:
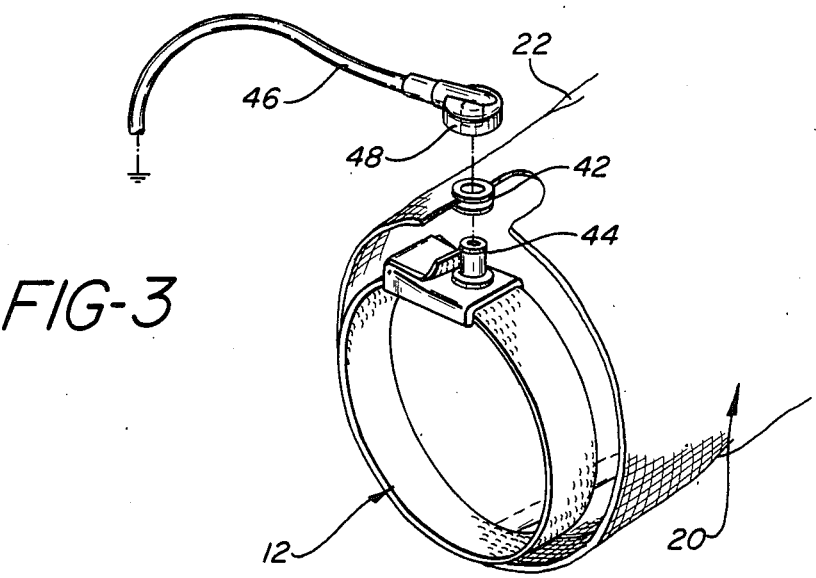
FIG. 3 is still another embodiment of such a device.

FIGS. 2 and 3 show two other embodiments of this invention.

In FIG. 2 two male snap connecting mean 28, 29 are provided on wristlet 12 and a female snap connecting means 30 is provided on sleeve 22. Electrical connecting cord 32 is provided, one end of which has a female snap connecting means 34 and the other end of which has a male snap connecting means 36. The snap connecting means 34, 36 mate respectively with the snap connecting means 29 on the wristlet 12 and the snap connecting means 30 on the sleeve 22. A grounding cord 38 is provided with a snap means 40 which mates with snap 28 on wristlet 12.

FIG. 3 shows another embodiment wherein a conductive eyelet 42 is provided at the end of sleeve 22. Attached to wristlet 12 is a male member 44 which matingly fits through eyelet 42 and is in electrical contact therewith. A grounding cord 46 is provided, one end of which has a female snap 48 thereon which mates with male member 44 to provide an electrical connection therewith and maintain member 44 secure in eyelet 42.

Figure 4:
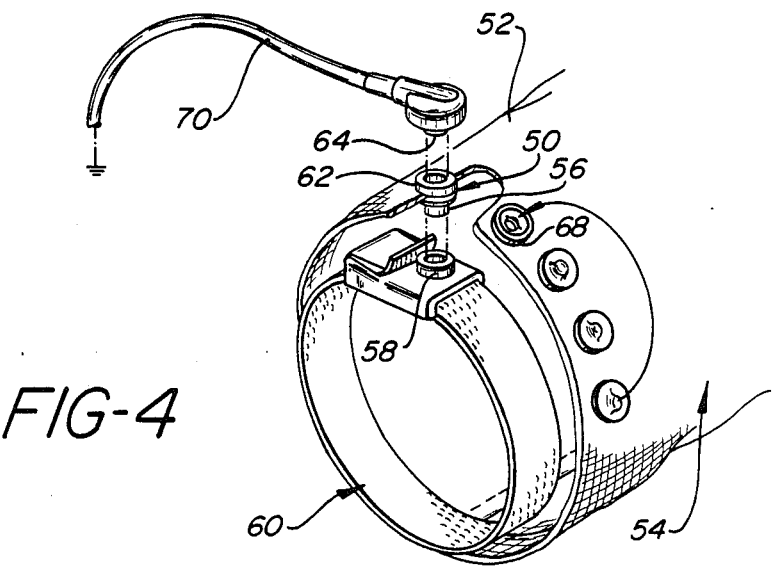
FIG. 4 shows still another embodiment of this invention.

In connection with the embodiment shown in FIG. 3 it is also possible to use what is known as a "gypsy" stud and socket arrangement which reduces in half the number of components necessary for snap fastening. FIG. 4 shows such an embodiment. In this embodiment a "gypsy" type stud and socket snap fastener 50 replaces the eyelet 42 construction used in FIG. 3. Fastener 50 secures the grounding wire 70 and the wristband 60 to sleeve 52. A "gypsy" type stud and socket 50 are fastened to the sleeve 52 of the garment 54. The "stud" side 56 engages and mates with a standard snap receptacle 58 disposed on the wristband 60. The other side 62, i.e. the "socket", of the "gypsy" type stud and socket 50 is disposed on the outer portion of the sleeve 52 adapted to mate with a male snap component 64 of standard configuration which is attached to grounding wire 70. Preferably, as depicted in FIG. 4, the sleeve of the garment has four additional snaps used for size adjustment of the sleeve. As shown in FIG. 4, there is one female snap 68 and three male stud portions 72. The female 68 portion will be positioned near the top of the sleeve as worn by the user, i.e. on the top of the wrist, so that the sleeve 52 can be gathered up from around the bottom of the sleeve 52 so that the connection of the grounding cable 70 will be on the top of the wrist area of the user. This prevents cable 70 from interfering with the activities of the wearer of the garment.

In all the embodiments depicted, provision may be made for attaching the wristlet to the sleeve of the garment on both sleeves to accommodate for right handed and left handed people.

Optionally, but not shown, the end of the sleeves may have an elastic band therein to cause the sleeve end to act as a wristlet. The sleeve is then grounded by an appropriate wire connection.

In each of the embodiments a current limiting resistor having a normal ohmic value of 1 megohm is incorporated into the grounding circuit.

While the fastener for the various conductive means has been described here as snaps, it should be noted that any other convenient type of fasteners may also be used, where applicable. So for example, alligator clips or other types of fasteners are also capable of being used in various aspects of this invention.

It should be pointed out that, typically, there is no continuous contact between the static protective garment and the skin of the wearer other than the conductive pathway produced by this invention. Typically, the static protective garment only comes in contact with the clothing worn by the user. However, because of the conductivity of the static protective garment, any electro-static charges which are developed due to the interaction of the clothing of the wearer between layers thereof and/or the skin of the wearer and the clothing are transferred to the static protective garment either by direct contact of the clothing to the garment or the deliberate contact between the skin of the wearer and the static protective garment by means of the grounded pathway created by this invention.

From the foregoing embodiments it can be seen that the objects of this invention are achieved by providing a simple and inexpensive device and method for simultaneously and continuously grounding both the person and the anti-static garment being worn.

I claim:

1. A device for dissipating electro-static electricity from a person wearing a static protective garment comprising:

a means for continuously conducting electricity between the garment and the person including a conductive wristlet to be worn by the person having means for conducting electricity between the wristlet and a sleeve of the garment, a conductive fastener on said wristlet, a conductive fastener on said sleeve which conductively mates with said conductive fastener on said wristlet, and a means for continuously conducting electricity from the garment or person to a ground.

2. The device of claim 1, wherein the conductive fasteners on said sleeve and wristlet are adapted to be conductively connected to each other by a conductive cord having a conductive fastener on each end, one end of which connects with the fastener on the sleeve and the other end of which connects with the fastener on the wristlet.

3. The device of claim 1, wherein the conductive fastener on the sleeve is an eyelet and the conductive fastener on the wristlet is a male snap member which matingly passes through the eyelet and is in electrical contact therewith, and wherein the means for continuously conducting electricity from the garment to a ground is a conductive cord having a conductive snap on one end which conductively mates with the male fastener member to secure the male fastener member in the eyelet.

4. The device of claim 1, wherein the conductive fastener on the sleeve has a stud on one side and a socket on the other, and the conductive snap on the wristlet mates with a side of the conductive snap on the sleeve, and wherein the means for continuously conducting electricity from the garment to a ground is a conductive fastener, a conductive cord having one end which conductively mates with the other side of the conductive fastener on the sleeve.

5. The device of claim 2, wherein the means for continuously conducting electricity from the garment to a ground is a conductive cord having a conductive fastener on one end which conductively mates with another conductive fastener on the wristlet.

6. The device of claim 1, wherein the means for continuously conducting electricity from a garment to a ground is a conductive cord having a conductive fastener on one end which conductively mates with another conductive fastener on the wristlet.

* * * * *